US007260436B2

(12) United States Patent
Kilgore et al.

(10) Patent No.: US 7,260,436 B2
(45) Date of Patent: Aug. 21, 2007

(54) IMPLANTABLE NETWORKED NEURAL SYSTEM

(75) Inventors: Kevin L. Kilgore, North Olmsted, OH (US); Paul Hunter Peckham, Cleveland Heights, OH (US); Timothy J. Crish, Stongsville, OH (US); Brian Smith, Cleveland Heights, OH (US)

(73) Assignee: Case Western Reserve University, Cleveland, OH (US)

( * ) Notice: Subject to any disclaimer, the term of this patent is extended or adjusted under 35 U.S.C. 154(b) by 636 days.

(21) Appl. No.: 10/272,484

(22) Filed: Oct. 16, 2002

(65) Prior Publication Data

US 2003/0139783 A1 Jul. 24, 2003

Related U.S. Application Data

(60) Provisional application No. 60/329,721, filed on Oct. 16, 2001.

(51) Int. Cl.
*A61N 1/08* (2006.01)
(52) U.S. Cl. .............................. 607/60; 607/2; 607/48; 607/49
(58) Field of Classification Search ............ 607/39–49, 607/53–55, 60; 623/11.11, 25
See application file for complete search history.

(56) References Cited

U.S. PATENT DOCUMENTS

| | | | | |
|---|---|---|---|---|
| 4,494,950 A | | 1/1985 | Fischell | |
| 4,524,774 A | * | 6/1985 | Hildebrandt | ................. 607/62 |
| 4,697,808 A | * | 10/1987 | Larson et al. | ................. 482/51 |
| 4,799,487 A | * | 1/1989 | Bleicher | ...................... 607/48 |
| 5,167,229 A | | 12/1992 | Peckham et al. | ........... 128/421 |
| 5,193,540 A | | 3/1993 | Loeb et al. | |
| 5,324,316 A | * | 6/1994 | Schulman et al. | ............ 607/61 |
| 5,814,089 A | * | 9/1998 | Stokes et al. | ................. 607/32 |
| 5,999,848 A | | 12/1999 | Gord et al. | .................... 607/2 |
| 6,141,588 A | * | 10/2000 | Cox et al. | ....................... 607/9 |
| 6,164,284 A | | 12/2000 | Schulman et al. | .......... 128/899 |
| 6,185,452 B1 | | 2/2001 | Schulman et al. | |
| 6,315,721 B2 | | 11/2001 | Schulman et al. | .......... 600/301 |
| 6,358,202 B1 | * | 3/2002 | Arent | ......................... 600/300 |
| 6,564,807 B1 | * | 5/2003 | Schulman et al. | .......... 128/899 |

OTHER PUBLICATIONS

Kobetic et al., "Synthesis of Paraplegic Gait with Multichannel Functional Neuromuscular Stimulation", IEEE Transactions On Rehabilitation Engineering, vol. 2, No. 2, Jun. 1994.
Popovic et al. "Optimal Control of Walking with Functional Electrical Stimulation: A Computer Simulation Study", IEEE Transactions On Rehabilitation Engineering, vol. 7, No. 1, Mar. 1999.
Skelly et al., "Real-Time Gait Event Detection for Paraplegic FES Walking", IEEE Transactions On Rehabilitation Engineering, vol. 9, No. 1, Mar. 2001.

* cited by examiner

*Primary Examiner*—George Manuel
*Assistant Examiner*—Nicole R. Kramer
(74) *Attorney, Agent, or Firm*—Renner, Otto, Boisselle & Sklar, LLP (57) ABSTRACT

A neural prosthesis includes a centralized device that can provide power, data, and clock signals to one or more individual neural prosthesis subsystems. Each subsystem may include a number of individually addressable, programmable modules that can be dynamically allocated or shared among neural prosthetic networks to achieve complex, coordinated functions or to operate in autonomous groups.

21 Claims, 8 Drawing Sheets

IMPLANTABLE NETWORKED NEURAL SYSTEM

RELATED APPLICATIONS

This application claims the benefit of U.S. Prov. App. No. 60/329,721, filed on Oct. 16, 2001. The entire contents of that application are incorporated herein by reference.

BACKGROUND OF THE INVENTION

Neurological trauma, dysfunction or disease can leave persons with severe and life threatening motor or sensory disabilities that can compromise the ability to control basic vital functions. Persons with neurological impairments often rely on personal assistants, adaptive equipment and environmental modifications to facilitate their daily activities. Neural prostheses are highly effective methods for restoring function to individuals with neurological deficits by electrically manipulating the peripheral or central nervous systems. By passing small electrical currents through a nerve, neural prostheses can initiate action potentials that eventually trigger the release of chemical neurotransmitters to affect an end organ or another neuron. Techniques exist to selectively activate axons of any size or location within a nerve or fascicle, making it possible to preferentially target small sensory fibers or duplicate natural motor unit recruitment order to minimize fatigue and grade the strength of a stimulated muscular contraction. In addition to exciting the nervous system, the proper current waveform and configuration of electrodes can block nerve conduction and inhibit action potential transmission. Thus, in principle any end organ normally under neural control is a candidate for neural prosthetic control.

Neural prosthetic devices that electrically stimulate paralyzed muscles provide functional enhancements for individuals with spinal cord injury and stroke such as standing and stepping, reaching and grasping, and bladder and bowel function. Current implanted neural prosthetic systems utilize considerable external powering and signal processing, and each system is tailored to the specific application for which it was intended. The need to design a customized implant system for each application severely limits progress in the field and delays introduction of new technology to the end user.

Generally, neural prostheses consists of both external and implanted components. External components consist of sensing apparatus, signal processing, and transmission to an internal implanted component. The internal component receives the externally transmitted signal and generates appropriate stimuli in response to the signal. The internal components might also include sensors, which measure some internal variable and transmit the signal to the external apparatus for processing.

Implanted neural prostheses have been successfully applied to the sensory (e.g., cochlear and visual prostheses) and motor (i.e.hand grasp) systems, as well as to the viscera (e.g., micturition, defecation) and central nervous system (e.g., deep brain stimulation).

In further advancements of neural prostheses, a number of sensors and actuators have been combined into networks that cooperate to extend a neural prosthesis over an area of the body, with nodes of the network operating under control of a central controller. Such networks are described, for example, in U.S. Pat. No. 5,167,229 to Peckham, et al.

It is clear that neural prosthetic approaches can provide both therapeutic and functional benefits to individuals with impairments due to neurological injury or disorder. However, as a significant disadvantage prior neural prostheses typically provide only crude networking capability and limited, if any, programmability at nodes within the prosthetic network. Despite the promise of neural prostheses, there remains a need for a an architecture that is sufficiently open and flexible to permit the implementation of complex and varying prosthetic functions, and to invite the design of a wide range of sensors and actuators for use therewith.

SUMMARY OF THE INVENTION

A neural prosthesis may include a centralized device that can provide power, data, and clock signals to one or more individual neural prosthesis subsystems. Each subsystem may include a number of individually selectable, programmable modules that can be dynamically allocated or shared among neural prosthetic networks to achieve complex, coordinated functions or to operate in autonomous groups.

In one aspect, the invention is an implantable system including a plurality of modules implantable in living tissue, each module including at least one of a sensor or an actuator, a processor, and a network interface configured to communicate with at least one other one of the plurality of modules; and a power source providing a data signal, and a power signal to each one of the plurality of modules, each module obtaining power from the power signal.

The power source may further provide a clock signal. The clock signal may be a variable system clock signal modulated onto the power signal for controlling power consumption by one or more of the plurality of modules. The nervous system may include at least one of sensory nerves, motor nerves, and neural circuits.

The data signal may include control information for at least one of the plurality of modules. The data signal may be addressable to one or more selected ones of the plurality of modules. One of the plurality of modules may modulate a data signal onto the power signal.

In another aspect the invention is a system including a first neural prosthesis controlling a nervous system in a first region of a body, a second neural prosthesis controlling the nervous system in a second region of the body; and a controller connected in a communicating relationship with the first neural prosthesis and the second neural prosthesis, the controller coordinating a transfer of data between the first neural prosthesis and the second neural prosthesis to achieve a body function that combines the first region of the body and the second region of the body.

The communicating relationship may include a data network having a data transmission rate of at least 100 kbps. The communicating relationship may include a wireless network. The body function may include walking. The body function may include a muscle contraction in the first region in response to a user-initiated movement detected in the second region.

The system may include one or more additional neural prostheses. The one or more additional neural prostheses may be connected in a communicating relationship with the controller, or with the first neural prosthesis or the second neural prosthesis.

In another aspect, the invention is a system including a power supply packaged for implantation into a cavity of a body, the power supply including a rechargeable power source, a port configured to couple the rechargeable source to a charger that is external to the body cavity, and control circuitry, the control circuitry configured to generate a power signal from the rechargeable power source, the power signal being a charge-balanced signal, the control circuitry further configured to modulate a clock signal onto the power signal, and to modulate a data signal onto the power signal, thereby providing a modulated power signal; and a plurality of leads extending from the power supply and carrying the modulated power signal, the leads being biocompatible leads adapted for connection to one or more power draining devices.

The plurality of leads may include a pair of leads for each limb of the body that contains power draining devices, each plurality of leads carrying a different modulated power signal. The port may include a radio frequency transcutaneous link for coupling to the charger. The rechargeable source of direct current may include a battery. The battery may be at least one of a nickel cadmium battery, a lithium ion battery, and a nickel-metal hydride battery. The power supply may include a 500 mW power supply.

The system may further include a controller that controls operation of the power supply and a communication link for maintaining communications between the controller and an external device. The controller may download programming information through the communication link. The programming information may control operation of the power supply. The programming information may control operation of a device connected to one or more of the plurality of leads. The communication link transmits at least one of test information and diagnostic information between the controller and the external device. The communication link may transmit sensor data to the external device. The communication link may transmit a user input to the controller.

In another aspect, the invention is device including at least one of a sensor or an actuator, a processor, a network interface coupled to the processor and the at least one of a sensor or an actuator, the network interface adapted for connection to a network, and including circuitry to receive power from a power signal provided over the network, and to demodulate a clock signal and a data signal from the power signal, and a housing that encloses at least a portion of the at least one sensor or actuator, the network interface, and the processor, the housing formed of a biocompatible material, and shaped and sized for implantation into a body.

The network interface may modulate a data signal onto the power signal. The processor may be at least one of a microprocessor, a microcontroller, or a programmable digital signal processor. The network interface may maintain communications using at least one of the CAN protocol or the MICS protocol. The sensor or actuator may include a sensor selected from the group consisting of an electroencephalogram sensor, an electromyogram sensor, an electrooculogram sensor, an electroneurogram sensor, and a three-dimensional accelerometer. The sensor or actuator may include a sensor for sensing at least one of pressure, finger contact, joint angle, limb segment velocity, or temperature. The sensor or actuator may include an actuator includes an actuator selected from the group consisting of a nerve stimulator, a blocking cuff-electode nerve stimulator, and drug delivery device.

In another aspect, the invention is a device including a first network interface connected in a communicating relationship with a first neural prosthetic that autonomously controls a nervous system of a first region of a body, the first network interface configured to provide a first power signal, a first data signal, and a first clock signal to the first neural prosthetic; a second network interface connected in a communicating relationship with a second neural prosthetic that autonomously controls the nervous system of a second region of the body, the second network interface configured to provide a second power signal, a second data signal, and a second clock signal to the second neural prosthetic; a controller that selectively passes data from the first neural prosthetic to the second neural prosthetic; and a housing that encloses at least a portion of the first network interface, the second network interface, and the controller, the housing formed of a biocompatible material and shaped for implantation into a body.

The controller may selectively pass data from the second neural prosthetic to the first neural prosthetic. The data signal may be modulated onto the power signal. The clock signal may be modulated onto the power signal. The network interface may employ a wired communication medium. The network interface may employ a wireless communication medium. The controller may generate control information to coordinate body function in each of the first neural prosthetic and the second neural prosthetic. The device may further include one or more additional neural prosthetic networks.

In another aspect, the invention is a system including a plurality of devices, each one of the plurality of devices being a biocompatible, implantable device that shares a communication medium, the plurality of devices grouped into one or more networks across the communication medium wherein devices in a network operate autonomously to control a body function; and a controller that dynamically reallocates one or more of the devices among the one or more networks to perform a different body function.

The controller may be a programmable controller coupled to the communication medium. The controller may be distributed among programmable processors operating on each one of the plurality of devices. More than one of the networks may share one of the plurality of devices. The communication medium may include at least two branches that are physically separated from one another by a bridge. At least one of the networks includes a device from each of two or more of the at least two branches, control data within the at least one of the networks being communicated through the bridge.

BRIEF DESCRIPTION OF THE DRAWINGS

The invention is pointed out with particularity in the appended claims. The advantages of the invention may be better understood by referring to the following description taken in conjunction with the accompanying drawing in which:

DETAILED DESCRIPTION OF CERTAIN EMBODIMENTS

To provide an overall understanding of the invention, certain illustrative embodiments will now be described, including neural prostheses deployed for therapeutic use in humans. However, it will be understood that the methods and systems described herein can be suitably adapted to other applications and environments where control or monitoring of a nervous system, either human or non-human, may be usefully employed. All such variations are intended to fall within the scope of the invention described below.

In the following description, corresponding reference characters indicate corresponding components throughout the several views of the drawings, unless specifically indicated otherwise.

Figure 1:
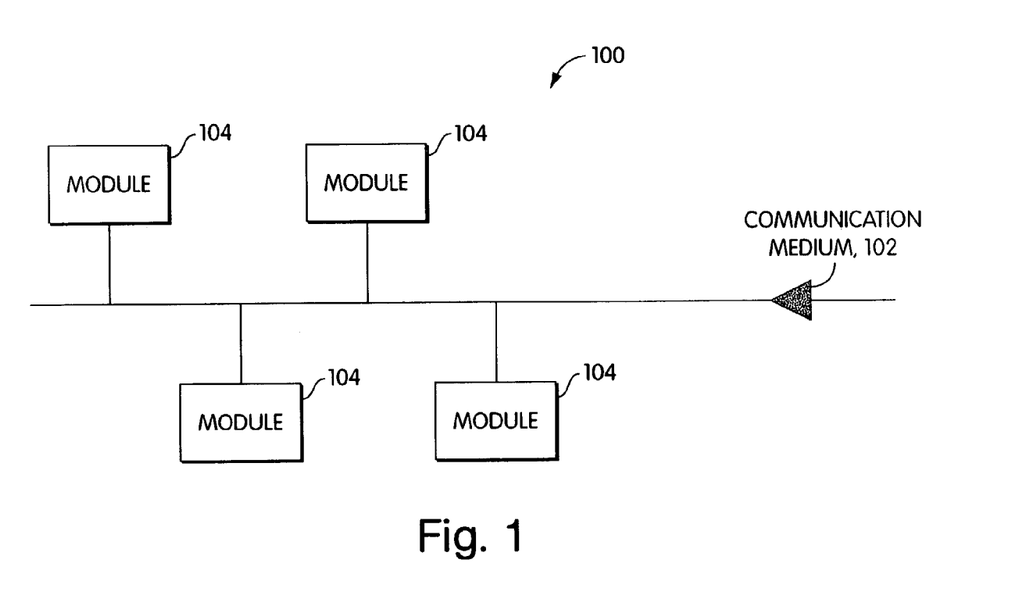
FIG. 1 is a block diagram of a neural prosthesis.

FIG. 1 is a block diagram of a neural prosthesis. The neural prosthesis 100 includes a communication medium 102 and a number of modules 104. The modules 104 may include sensors and/or actuators, and may be implanted in any distributed fashion throughout a body. Although four modules 104 are shown in FIG. 1, the neural prosthesis 100 may include more or fewer modules 104.

Each module 104 may be linked to the communication medium 102, which may be, for example, any electrically conductive material, such as a copper wire encased in a biocompatible rubber or plastic insulator, or a plurality of leads encased as a cable in a coaxial, twisted pair, or ribbon configuration. The communication medium 102 may distribute a power signal, a clock signal, and a data signal to the modules 104, either through one physical network or through a number of coextensive physical networks.

In one embodiment, power is distributed with an alternating current signal, which may reduce tissue damage as well as corrosion of metal components in a biological environment. The clock signal and the data signal may be modulated onto the alternating current power signal using any suitable modulation scheme. For example, clock data may be conveyed in a frequency of the power signal, and data may be modulated onto the clock/power signal using amplitude shift keying. Currently popular protocols that may be used for communicating data in a neural prosthesis include variations of Ethernet, Universal Serial Bus ("USB"), and Firewire.

In another embodiment, the communication medium 102 may include wired and wireless portions. For example, the power signal and a clock signal may be distributed through a wired portion of the communication medium 102, using a clock signal modulated onto an alternating current power signal as described above. The data signal may be wirelessly communicated using any suitable short-range wireless communications system that propagates signals using radio frequency or other electro-magnetic carriers. One example of such a protocol is the Medical Implant Communication Service ("MICS"), a recently FCC approved system for wireless communications into or out of a body in a medical environment. Any other standard or proprietary wireless system suitable for use with the devices described herein may similarly be employed. The data signal may instead be distributed using any ultrasonic carrier frequency, such as a one-hundred kilohertz sonic signal, or other techniques employing mechanically transmitted energy. The data signal may also be distributed using a Personal Area Network ("PAN") in which the human body is used as a conductor to capacitively couple small currents among network elements.

In another embodiment, the communication medium 102 may be entirely wireless, with each module 104 supplying its own power through a battery or other rechargeable or renewable power source. Power-up and power-down signals, as well as a controllable system clock, may be transmitted throughout the wireless communication medium 102 to permit power management within the neural prosthesis 100, and portions thereof, in the absence of power distribution through the wired communication medium 102.

One network protocol that may be usefully deployed in the neural prosthesis 100 is the Controller Area Network ("CAN") protocol. This is an ISO standard (ISO 11898) for serial communications, originally developed for networking automobile components, and more recently finding broad application in industrial automation and control systems. The protocol defines the physical layer and the data-link layer of the Open Systems Interconnection ("OSI") Reference Model, and provides for arbitration and error handling in a peer network that shares a physical communication medium. A number of microcontrollers have been designed specifically for use with the CAN protocol, and may be usefully deployed with the neural prosthesis 100 described herein, such as Atmel's T89C51CC01/02 microcontrollers. High-level protocols (e.g, application protocols) have been designed specifically for use with the CAN protocol to address matters such as start-up behavior, flow control, and status reporting within the CAN-based network. In one embodiment of the neural prosthesis, the physical layer and data link layer used with the communication medium 102 are defined by the CAN protocol with a communication rate of 100 kilobits per second ("kbps").

Figure 2A:
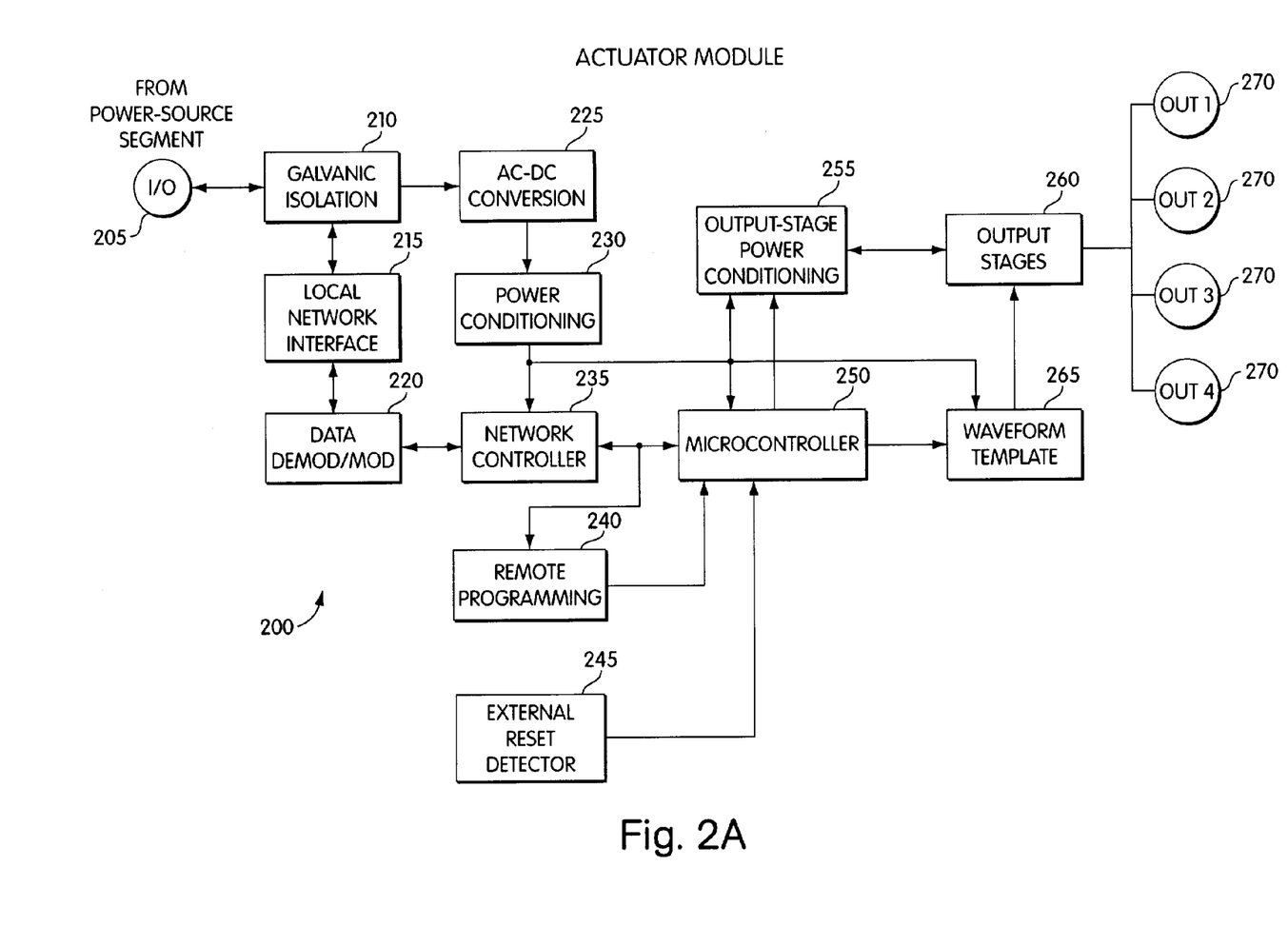
FIG. 2A is a block diagram of an actuator module that may be used in a neural prosthesis.

FIG. 2A is a block diagram of an actuator module that may be used in a neural prosthesis. The module 200, which may be one of the modules 104 of FIG. 1, may include a network input/output 205, galvanic isolation unit 210, a local network interface 215, a data modulator/demodulator 220, an AC/DC conversion unit 225, a power conditioning unit 230, a network controller 235, a remote programming unit 240, an external reset unit 245, a microcontroller 250, an output-stage power conditioner 255, one or more output stages 260, a waveform template 265, and one or more outputs 270. It will be appreciated in the following discussion that, while described separately, certain of the above components may be integrated into a single semiconductor device or chipset. It will similarly be appreciated that certain of the components may instead be realized as discrete analog and digital circuitry. All such realizations are intended to fall within the scope of the systems described herein.

The network input/output 205 physically connects the module 200 to a power/data network, such as the communication medium 102 of FIG. 1. This may be any tap or plug connector, preferably one that seals the connection from surrounding tissue and/or body fluids when implanted.

The galvanic isolation unit 210 may serve to physically isolate electronics within the module 200 from the network (not shown) to which the module 200 is connected. The galvanic isolation unit 210 may include, for example, a transformer for inductively coupling electrical signals within and without the module 200. In addition to decoupling of electro-magnetic noise generated by the module 200 from the network, isolation may be used as a safety feature in biological instrumentation systems to prevent accidental leakage of power or other signals into the biological medium.

The local network interface 215 may include circuitry to detect and recover a clock signal and a data signal from a signal received through the input/output 205. The local network interface 215 may be a bi-directional interface capable of receiving or transmitting a data signal. The data demodulator/modulator 220 may operate on a physical signal to add or remove data using, for example, amplitude shift keying or any other modulation scheme capable of sharing the network with a clock signal. The clock signal may be obtained directly from the data carrier, or may be derived from the data carrier signal using, for example, a phase-locked loop or other frequency control circuitry. In certain wireless embodiments of the systems described herein, the module 200 may include clock generation circuitry such as oscillators and/or other tuned circuits to independently generate local clock signals.

The network controller 235 may implement any communications protocol suitable for a neural prosthesis. The network controller 235 may reside physically on the same semiconductor device as a microcontroller where, for example, a commonly used protocol has microcontrollers built specifically to implement the protocol. For example, commercially-available microcontrollers such as Atmel's T89C51CC01/02 fully implement the physical layer and data link layer of CAN. This and other widely-used protocols may also be realized in digital signal processors, processors, and microcontrollers. Optionally, these or other network protocols may be realized using other semiconductor integration technologies such as custom-designed Application Specific Integrated Circuits, with or without additional programmability or application logic, and other programmable devices such as Programmable Gate Arrays or Programmable Logic Devices. Any such realization of the network controller 235 is intended to fall within the scope of the description provided herein.

The Alternating Current/Direct Current ("AC/DC") conversion unit 225 begins a power signal path within the module 200, as distinct from the data signal and clock signals demodulated therefrom. The AC/DC conversion unit 225 rectifies an alternating current signal received from the network into a direct current. The power conditioning unit 230 further conditions the signal to remove ripples in the direct current signal and regulate the voltage such that it is suitable for use with the analog and digital circuits and devices of the module 200. The AC/DC conversion unit 225 and the power conditioning 230 may be combined into a single circuit or semiconductor device, and may include any step-up or step-down conversion stages suitable for conforming the external network signal into an internal DC power signal for the module 200.

The microcontroller 250 may be any programmable device or devices suitable for controlling the neural prostheses, and may include one or more microcontrollers, microprocessors, application specific integrated circuits, programmable digital signal processors, programmable gate arrays, and/or programmable logic devices, as well as external volatile and/or non-volatile memory to support the operation thereof, such as Random Access Memory ("RAM"), Read-Only Memory ("ROM"), Programmable Read-Only Memory ("PROM"), Electrically Erasable Programmable Read-Only Memory ("EEPROM"), flash memory and so forth. Thus, the term "microcontroller" as depicted in FIG. 2A and described herein should be understood to include a number of devices capable of performing the functions described below. In certain embodiments, such as Atmel's T89C51CC01, the network controller 235 and programmable flash memory reside on the microcontroller chip as well. In general, the microcontroller 250 may have power consumption characteristics consistent with power supplies available in the network, and processing power adequate to receive and execute programming for use in a neural prosthesis.

A remote programming unit 240, which may be realized as a boot loader or other executable code on the microcontroller 250, detects program or firmware updates for the microcontroller 250 and manages reprogramming of the microcontroller 250 with the updated code. Updates may be incremental, involving replacement of a specified block or blocks of code stored in the microcontroller 250, or may include complete removal of all current code and replacement with new code received from the network. This capability may be employed, for example, to update waveforms that are stored in the waveform template 265. The remote programming unit 240 may also, or instead, permit reconfiguration of the module 200 and redeployment of the module 200 in a new or modified neural prosthetic network.

The external reset detector 245 provides for remote activation and de-activation of the module 200. A reset signal may be transmitted to the module 200 through any external stimulus, such as a fixed magnet placed near the module 200. While any type of signal may be used, including electrical signaling, magnetic signaling, or electro-magnetic signaling, or physical switching, the signal is preferably providing through some medium that is non-invasive, and does not require proper operation of any remaining components of the module 200.

The output-stage power conditioner 255 may be coupled to the power conditioning unit 230, and may include any circuitry for AC/DC conversion, DC/AC conversion, voltage step-up, voltage step-down, filtering, frequency modification, or any other signal conditioning required for operation of the outputs 270. Many actuators, for example, operate with thirty to forty Volts of DC power, which may require a significant step-up in voltage from the AC signal used on the network, as well as the DC power provided for other components within the module 200, which may operate in a range of, for example, three to five Volts.

The output stages 260 may provide further signal conditioning for one or more output signals to the outputs 270. This may include, for example, combining the power signal from the output-stage power conditioning unit 255 with one or more output waveforms from the waveform template 265. This may also include protection and isolation circuitry to protect a physical system that receives signals from the outputs 270, and to protect the internal circuitry of the module 200 from electrical transients in the physical system.

The waveform template 265 may reside in a volatile or non-volatile memory, either within the microcontroller 250 or external to the microcontroller 250. The waveform template 265 may operate, for example, as a look-up table of waveforms that may be applied by the microcontroller 250 to the outputs 270. The waveform may also, or instead, use linear and/or non-linear models to generate suitable waveforms which may be triggered by a signal from the microcontroller 250. The waveform template 265 may permit separation of program logic and actuator control. For example, program logic may dictate extension of a leg with a "move" command, while actuator control to achieve this result may entail a complex and time-varying series of neural signals and associated muscular contractions. As another example, certain effects and muscle responses are achieved by blocking neural signals that might otherwise be present. In this environment, signals to actuators may be based on empirical data or theoretical models describing biological relationships. In any case, the shape, amplitude, and duration of pulses to achieve a desired response may be stored as one or more waveforms in the waveform template 265. This functional separation may also permit a neural prosthesis to have actuators tailored to a particular recipient without any modification of the programming to achieve a gross effect, such as closing a hand.

The outputs 270 may include any actuators suitable for use in a neural prosthesis. In one embodiment, this includes one or more electrodes that may output stimulus, such as drive pulses stored in the waveform template 265. The outputs may stimulate nerve cells or some other portion of the nervous system, which in turn initiate a muscle contraction or body function. Outputs 270 may include, for example, nerve stimulators, blocking cuff-electrode nerve stimulators, or drug delivery devices.

The module of FIG. 2A may be hermetically sealed or otherwise housed in a biocompatible material, except where network connections 205 or outputs 270 require physical coupling to an external environment.

Figure 2B:
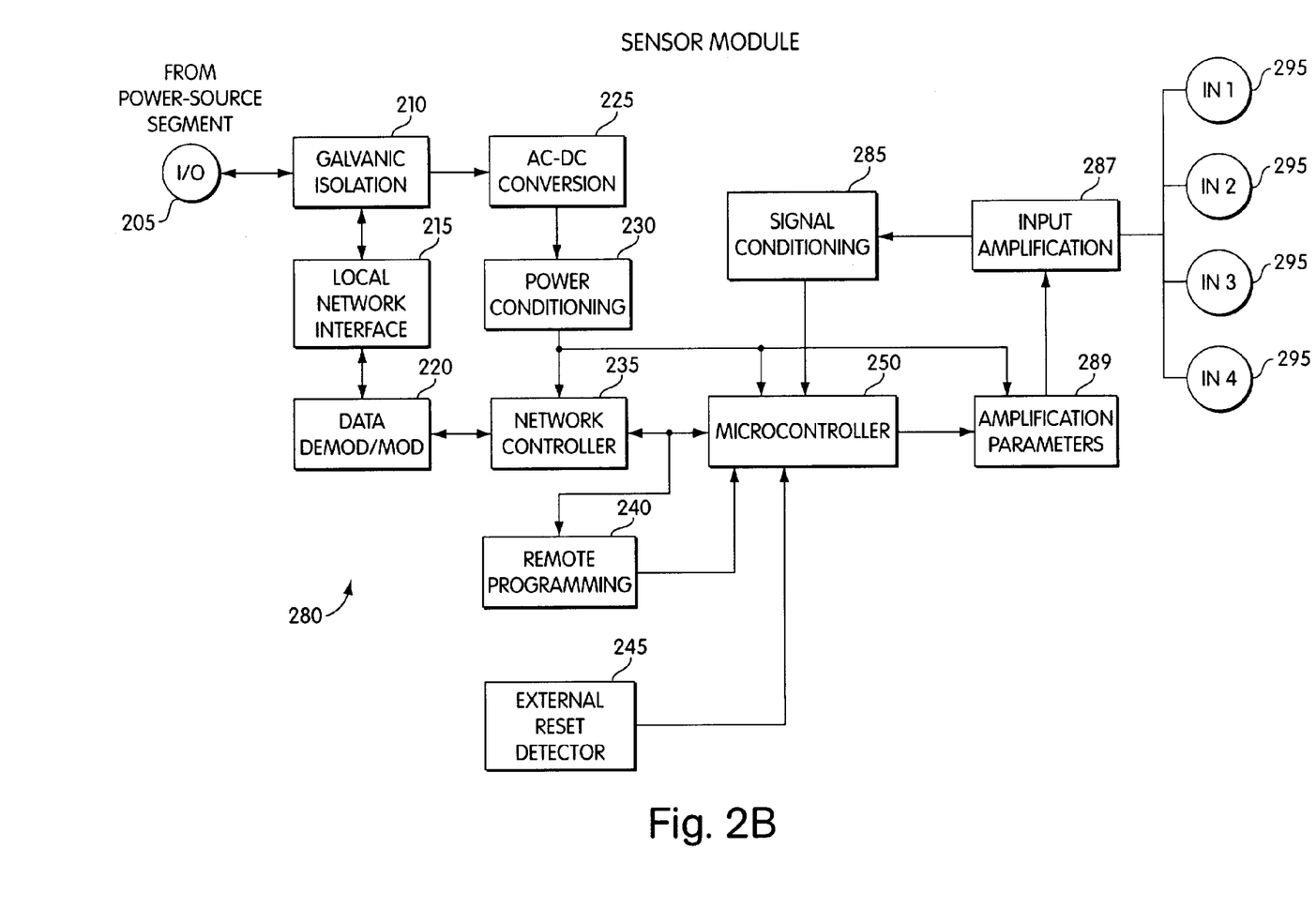
FIG. 2B is a block diagram of a sensor module that may be used in a neural prosthesis.

FIG. 2B is a block diagram of a sensor module that may be used in a neural prosthesis. Some of the components of the sensor module 280 may be the same as, or similar to, the components of the actuator module 200 described above. Thus it will be noted that the input/output 205, the galvanic isolation unit 210, the local network interface 215, the data demodulator/modulator 220, and AC/DC conversion unit 225, the power conditioning unit 230, the network controller 235, the remote programming unit 240, and external reset detector 245, and the microcontroller 250 may all be as described above with reference to FIG. 2A. The sensor module 280 may further include a signal conditioning unit 285, an input amplification unit 287, an amplification parameters unit 289, and one or more inputs 295, all described in greater detail below.

The one or more inputs 295 may include any type of sensor that may be usefully employed in a neural prosthetic. This includes, for example, biopotential sensors for electroencephalograms ("EEGs"), sensors for electromyograms ("EMGs"), sensors for electrooculograms ("EOGs"), three-dimensional accelerometer(s) that measure body orientation and motion, sensors for obtaining nerve recordings such as pressure or finger contact, and sensors for detecting physical quantities associated with physiology such as joint angle (through a variety of different transducers), limb segment velocity, temperature, $O_2$ content, glucose levels.

The input amplification unit 287 may serve to isolate an external medium from the electronics of the sensor module 280. The input amplification unit 287 may also perform various instrumentation functions, such as difference amplification of an input signal, filtering, sampling, and so forth.

The signal conditioning unit 285 may convert a signal received from the input amplification unit 287 (typically an analog signal) into a form suitable for storage and processing by the microcontroller 250 (typically a digital representation of the analog signal).

The amplification parameters unit 289 may store one or more parameters associated with the inputs 295, including, for example, calibration data for the inputs 295 or waveforms for use in matched filtering. The amplification parameters unit 289 may permit separation of program logic from calibration of the inputs 295 and associated functions, as described above with reference to the waveform template 265 of FIG. 2A.

Data gathered from the inputs 295, either in raw or processed form, may be stored in a buffer, which may be associated with the network controller 235 or the microcontroller 250, for transmission over the network. This data may be transmit periodically according to a schedule stored on the sensor module 280, or may be provided upon an external request for data received over the network.

In certain embodiments, one of the modules 104 of FIG. 1 may include one or more sensors as well as one or more actuators, provided there is not excessive interference between the signals of the two components.

Figure 3:
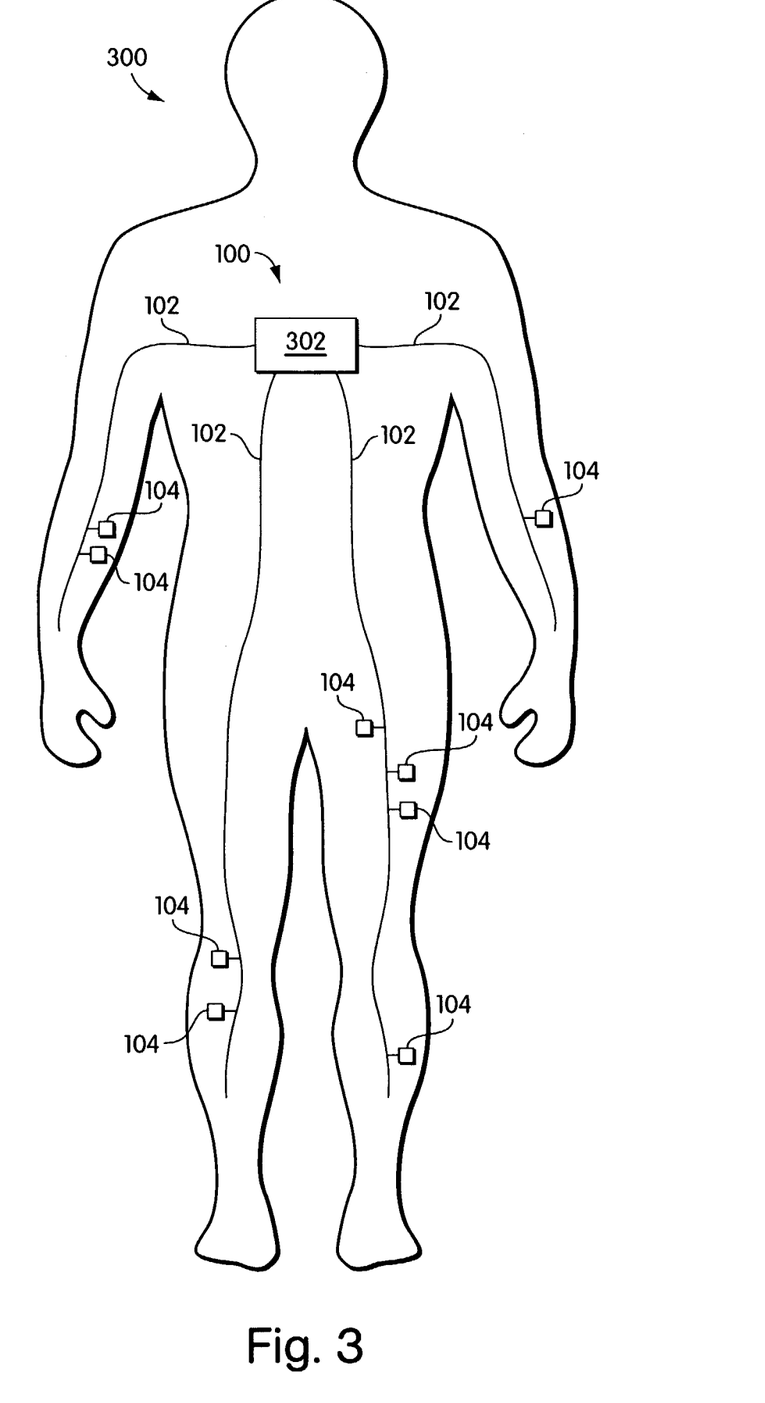
FIG. 3 shows a neural prosthesis implanted in a user.

FIG. 3 shows a neural prosthesis implanted in a user. The neural prosthesis 100 may include a number of physically separated communication mediums 102 or branches 102, each interconnecting one or more modules 104. A bridge 302 may interconnect the branches 102 of the neural prosthesis 100. As described in more detail below, this configuration may advantageously facilitate operation of autonomous networks along each branch 102, while permitting coordination of function across branches 102, or communications between modules 104 on different branches 102, all under control of the bridge 302. While nine modules 104 and four branches 102 are shown in FIG. 3, it will be appreciated that the neural prosthesis 100 may accommodate more or less branches 102, and more or less modules 104.

It should also be appreciated that independent networks may be formed within the neural prosthesis 100. These networks may be formed along branches 102 that define the physical topology of the neural prosthesis 100, or between and across branches 102 such that any two or more modules 104 within the neural prosthesis 100 may be grouped into a separate, virtual network to perform a desired function. It should also be appreciated, with reference to the programmability of the modules 104 described above, that the virtual networks may be dynamically re-allocated and reconfigured according to a desired function of the neural prosthesis 100.

More generally, control may be exercised autonomously over various regions of the body by defining a region and programming modules 104 within the region to operate autonomously. For example, one neural prosthetic network may be created for a left leg region, and another for a right leg region. Thus a complete neural prosthetic may be dynamically created for each region to be controlled. These networks may also communicate with one another through the communication medium 102 to achieve coordinated movements such as walking. Regions may instead be defined along functional lines, such as bladder or bowel control. It will further be understood that regions of the body need not be mutually exclusive, and may include overlapping or concentric physical regions within the body, according to the desired function of each neural prosthetic formed in this manner.

Figure 4:
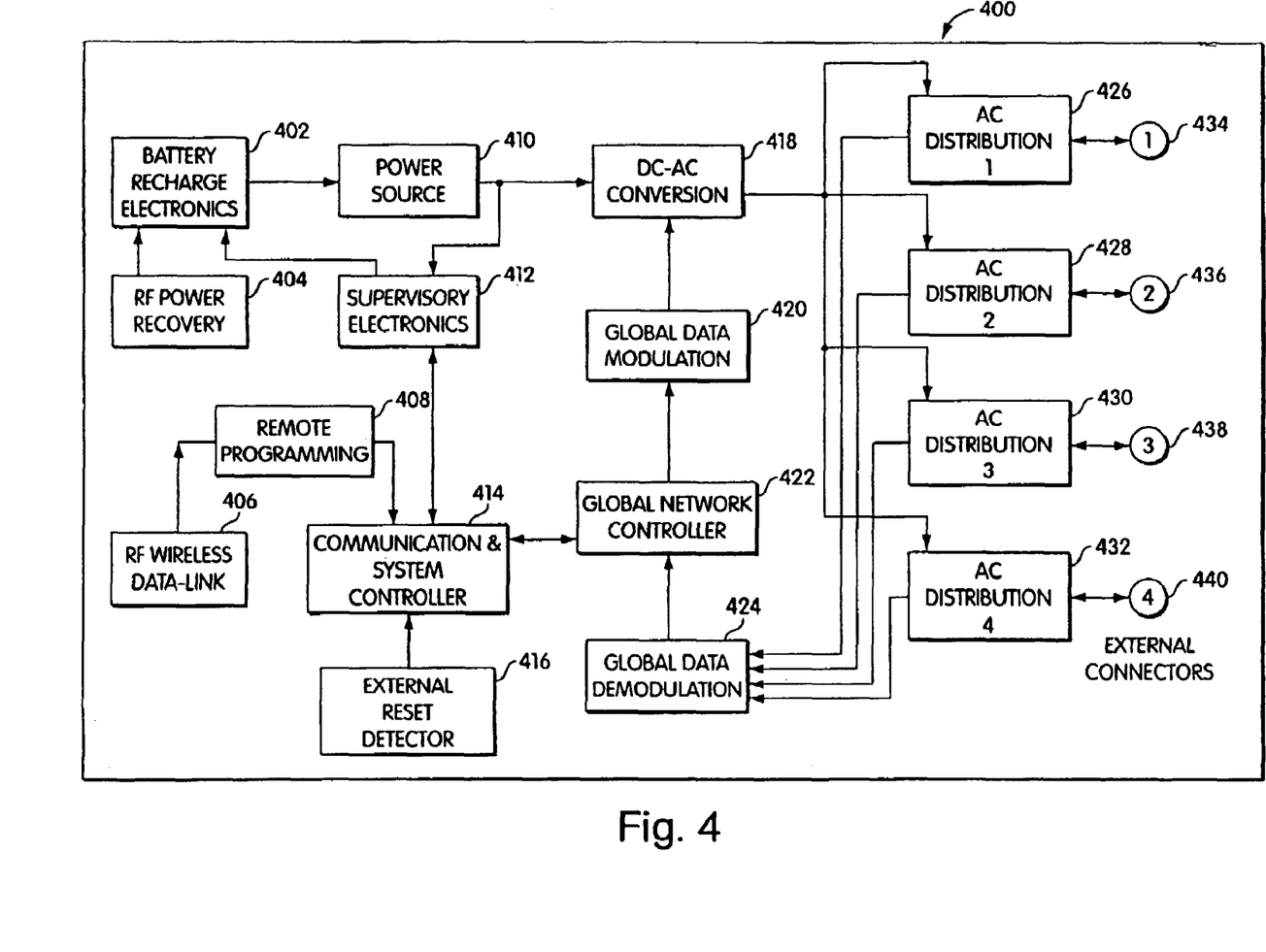
FIG. 4 is a block diagram of a bridge that may be used in a networked neural prosthesis.

FIG. 4 is a block diagram of a bridge that may be used in a networked neural prosthesis. The bridge 400, which may be the bridge 302 of FIG. 3, may include battery recharge electronics 402, a radio frequency power recovery unit 404, a radio frequency wireless data link 406, a remote programming unit 408, a power source 410, supervisory electronics 412, a controller 414, an external reset detector 416, a DC/AC conversion unit 418, a global data modulation unit 420, a global network controller 422, a global data demodulation unit 424, a number of distribution units 426-432, and a number of external connectors 434-440. It will be appreciated that, while four external connectors 434-440 are shown, more or less external connectors 434-440 may be used with a system as described herein, according to the number of separate physical networks connected to the bridge 400, and the expandability desired for the system.

The battery recharge electronics 402 receives power from the radio frequency power recovery unit 404, or port, and converts the recovered (AC) power into a form suitable for recharging the power source 410. The radio frequency power recover unit 404 may be a microstrip patch or antenna suitable for recovering power from a nearby, tuned radio-frequency source. The battery recharge electronics 402 may convert the recovered power into a steady, DC voltage, or a stream of pulses or other signal suitable for recharging the power source 410. The supervisory electronics 412 may monitor the charging status of the power source 410, and determine what recharging power should be delivered from the battery recharge electronics 402 to the power source 410. The supervisory electronics may implement safety features such as low power alerts and overcharge prevention, as well as other features to improve efficiency of the power source 410, extend the life of the power source 410, or otherwise manage power within the system.

The power source 410 may be, for example, a rechargeable power source that delivers 500 mW of continuous power. This may include batteries such as a lithium-ion battery, a nickel cadmium battery, or a nickel-metal hydride battery. The power source 410 may also include a renewable power source such as a fuel cell, and it will be appreciated that such a power technology will employ different supporting circuitry and physical apparatus than that depicted in FIG. 4.

The radio frequency wireless data link unit 406 may maintain a data link between the bridge 400 and an external system. The external system may, for example, provide programming for modules 104 connected to the neural prosthesis 100, or retrieve telemetry data from one or more sensor modules 200 connected to the neural prosthesis 100. While a radio frequency data link 406 is depicted in FIG. 4, it will be appreciated that any data link may be used, including any of the wireless communications techniques described above, as well as a percutaneous connections.

The remote programming unit 408 may detect programming data received over the data link maintained by the radio frequency wireless data link unit 406. As noted above, programming data may be for the bridge 400 or for a module 104 connected to one of the external connectors 434-440. Where the programming data is for the bridge 400, the remote programming unit 408 may manage loading of the programming data and re-initialization of the bridge 400. Where the programming data is for one or more of the modules 104, any transfer, loading, and execution of the programming data may be handled by the remote programming unit 408 or the controller 414.

The controller 414 may maintain external communications with the neural prosthesis 100, including the remote programming described above, as well as routine inquiries to the neural prosthesis 100 for diagnostics and data acquisition. The controller 414 may also communicate with the supervisory electronics 412 to control recharging of the power source 410, and to monitor a charge state of the power source 410. The controller 414 may also manage power throughout the neural prosthesis 100. For example, the controller 414 may generate power-up or power-down signals to specific modules 104 within the neural prosthesis 100, or the controller 414 may reduce a system clock rate to one or more of the external connectors 434-440 in order to conserve power in one or more branches 102 of the system that are in an idle or low activity state.

The controller 414 may also receive and process user inputs received through the wireless data-link 406, or through a separate percutaneous connection to the controller 414. These user inputs may be converted into control signals that are distributed to modules 104 of the neural prosthesis 100 through the external connectors 434-440.

The external reset detector 416 may receive an external reset signal through, for example, a wired connection to an external reset switch, or from a fixed magnet positioned near the external reset detector 416. When an external reset signal is received, the bridge 400 may be reset. Reset signals may also be transmitted over the branches 102 of the neural prosthesis 100 to all modules 104 connected thereto, or these devices may be reset through a separate, independent reset signal.

The DC/AC conversion unit 418 may convert the DC from the power source 410 into an AC form, or other charge-balanced signal, suitable to operate as a power signal for neural prosthesis 100. This AC signal may be globally managed to increase or decrease the clock signal modulated onto the AC signal. The clock signal may also be independently regulated for each branch 102 of the neural prosthesis 100 through the distribution units 426-432.

The global data modulation unit 420 may operate to modulate data onto the AC power signal provided by the DC/AC conversion unit 418. The global data demodulation unit 424 may demodulate data received from the branches 102 of the neural prosthesis, including, for example sensor and control data from modules 104 connected to the branches 102.

The global network controller 422, receives control data from the controller 414, and identifies a branch 102 for transmission of the data. This may include reprogramming data, requests for sensor data, or instructions to one or more modules 104 connected to one or more branches 102 of the neural prosthesis 100. The global network controller 422 may also perform a filtering function. In operation, network traffic on each branch 102 of the neural prosthesis may be reduced by confining traffic for that branch 102 to that branch 102. However, where a functional network of interoperating modules spans more than one branch 102, the global network controller 422 may listen at each branch 102 for traffic relating to the functional network and, where appropriate, pass data to one or more other branches 102. In this manner, operation of the neural prosthesis 100 may be coordinated across more than one branch 102 of the neural prosthesis.

The distribution units 426-432 and the external connectors 434-440 provide a physical interface to each branch 100 of the neural prosthesis 100 which may function in a similar manner to, for example, the input/output 205, galvanic isolation 210, and local network interface 215 of one of the modules 200, 280 of FIGS. 2A and 2B. It will be appreciated that one significant difference is that the distribution units 426-432 distribute power along a branch 102 of the neural prosthesis, while the input stages of a module 200, 280 extract power from the branch 102.

Figure 5:
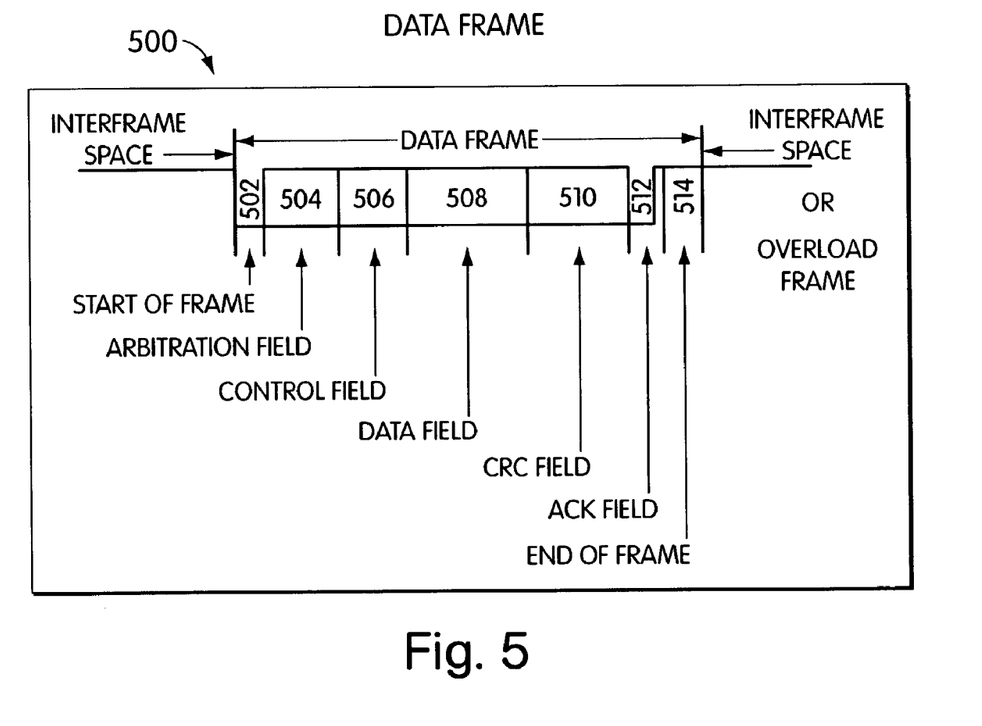
FIG. 5 is a block diagram of a data structure for communicating data in a neural prosthesis.

FIG. 5 is a block diagram of a data structure for communicating data in a neural prosthesis. The data structure 500 may include a start of frame 502, an arbitration field 504, a control field 506, a data field 508, a cyclic redundancy check field 510, an acknowledgement field 512, and an end of frame 514. This data structure 500 may be used to communicate between, for example, the controller 414 of the bridge 400 and individual modules 104 of the neural prosthetic 100. The data structure 500 also supports control and content specifiers that may be used to maintain communication between modules 104 so that one or more groups of modules 104 may be formed into a self-managing network to perform a desired function. The data structure 500 may also support reprogramming of one or more modules 104 through the communication medium 102 of the neural prosthetic 100.

The start of frame 502 includes one or more bits that signal the beginning of a message for communication within the neural prosthetic.

The arbitration field 504 includes a priority of the message, and specify a type of content for the message.

The control field 506 includes one or more bits that specify a length of the data field 508.

The data field 508 includes any data payload for communication within the neural prosthesis 100. This may include, for example, sensor data from a sensor module 200 in the neural prosthetic 100, actuator control data for controlling an actuator module 280 in the neural prosthetic 100, or programming data for programming a device 200, 280 in the neural prosthetic 100.

The cyclic redundancy check ("CRC") field 510 includes a CRC of data in the message, and may be used for error checking for messages communicated through the neural prosthetic 100.

The acknowledgement field 512 includes one or more bits signaling an acknowledgement request, or a reply to an acknowledgement request so that connection oriented messaging may be maintained among modules 104 of the neural prosthetic 100.

The end of frame 514 includes one or more bits that signal the end of the message.

It will be noted that the data structure 500 described above corresponds to the message specification for the CAN protocol. While this data structure is not dictated by the neural prosthetic 100 described herein, the data structure 500 does permit ready implementation with commercially-available electronics. Module-to-module addressing is not explicitly supported by the CAN protocol, which does not include a destination address. However, addressing may be effected within the broadcast messaging of CAN by, for example, placing address information within the data field 508, or by implying a destination module by the message type specified in the arbitration field 504. In this manner, each module 104 may communicate with each other module 104 through the neural prosthetic network.

Figure 6:
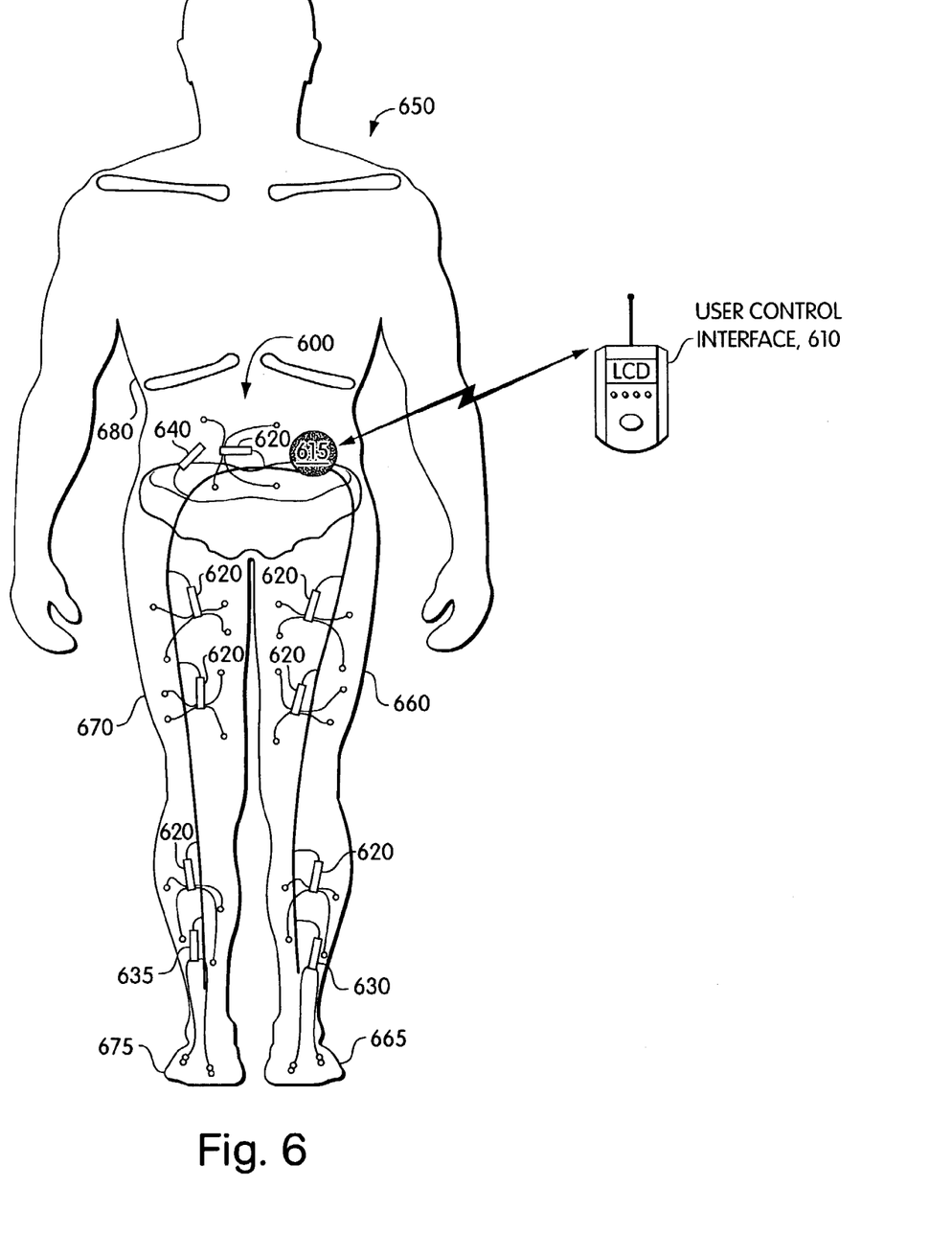
FIG. 6 shows a neural prosthesis for legs.

FIG. 6 shows a neural prosthesis for legs. The neural prosthesis 600 includes an external user interface 610, a bridge 615, one or more actuator modules 620, and one or more sensor modules 630-640. A recipient 650 may have a left leg 660 with a left foot 665, a right leg 670 with a right foot 675, and a torso 680. The prosthesis depicted in FIG. 6 may be used, for example, as an aid to a recipient 650 with lower limb paralysis. It will be appreciated that other arrangements, positioning, and combinations of modules may be used with a neural prosthesis for legs, and that the following example does not limit the scope of the systems described herein.

The actuator modules 620 may be positioned, for example within paralyzed muscles of the hips, the legs, and the ankles, as depicted generally in FIG. 6. Positioning of the actuator modules 620 may be refined for a particular prosthesis recipient according to, for example, where the actuator modules 620 will achieve the greatest recruitment of sensory nerves, motor nerves, and neural circuits of the nervous system, and muscles associated therewith. Positioning will also depend on which muscle groups will be used by the neural prosthesis 600.

A first sensor module 630 and a second sensor module 635 may be electroneurogram ("ENG") sensors that record nerve activity for the left foot 665 and the right foot 675 of the recipient 650.

A third sensor module 640 may include a three-dimensional accelerometer or other orientation sensor for monitoring orientation of the torso 680 of the user 650.

The user interface 610 may be a wireless, hand-held device or any other device suitable for communicating with the bridge 615 and receiving user input from the recipient 650. The user interface may display status information on a liquid crystal display, light-emitting diode display, or other display. Other status information, such as alarms, may be signaled through an audio output such as a speaker or a piezo-electric buzzer. User input may be received through, for example, a joystick, a keypad, one or more individual buttons, a microphone coupled to voice processing software, a touch pad, or any other input device. The user input may be packaged as a wearable wireless device or a band-held wireless device. Any other packaging convenient to the recipient 650 may also be employed.

Figure 7:
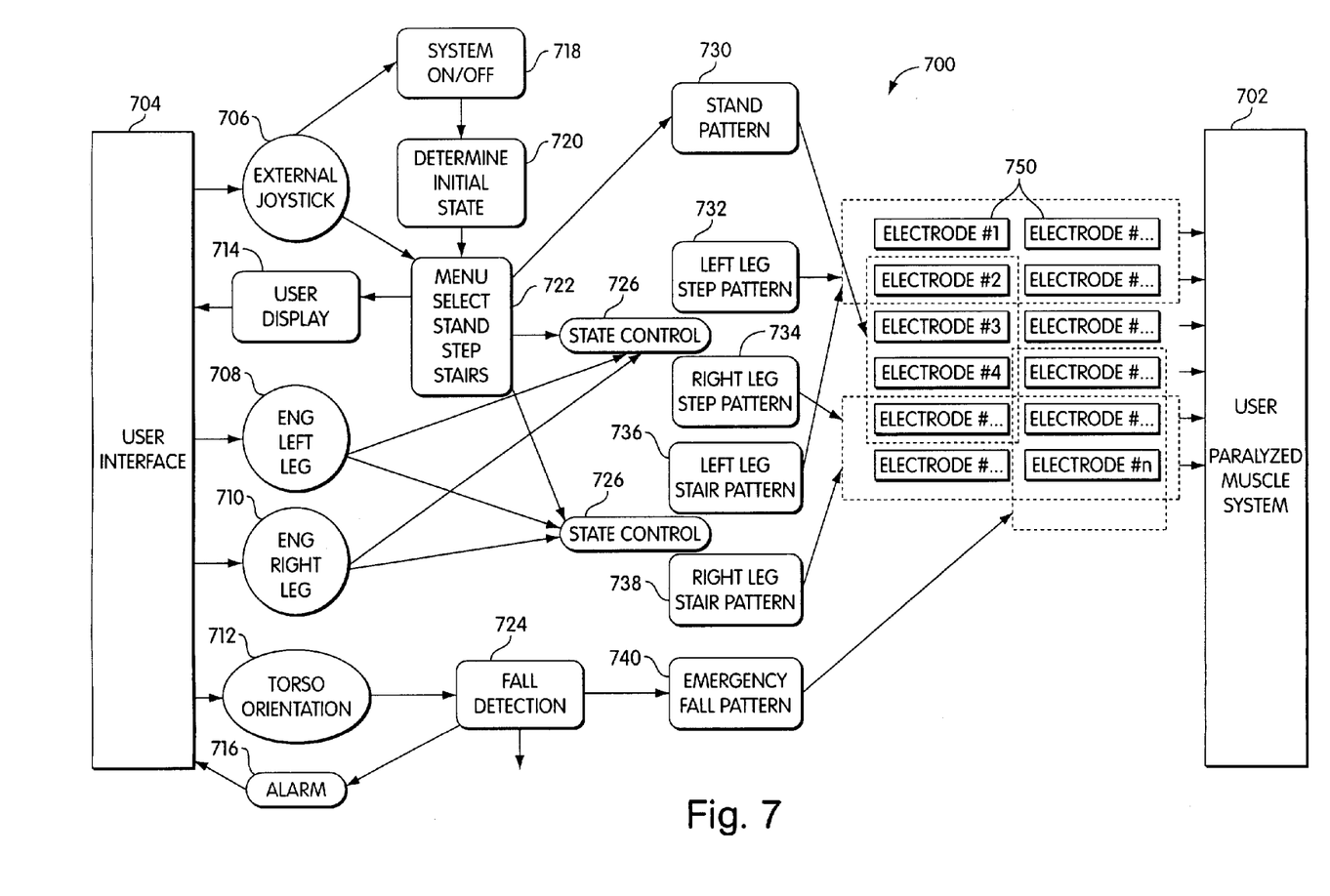
FIG. 7 depicts control of the neural prosthesis of FIG. 6.

FIG. 7 depicts control of the neural prosthesis of FIG. 6. As depicted the control system 700 permits a user to control a paralyzed muscle system 702 through a user interface 704. The system may include a joystick 706, a left leg sensor 708, a right leg sensor 710, a torso sensor 712, a user display 714, and an alarm 716. Processes executing on one or more modules 104 or a bridge 400 in the system may control states of operation, including a system on/off process 718, a determine initial state process 720, a menu process 722, a fall detection process 724, and one or more state control processes 726. The processes 718-726 may control one or more states of the system, including a stand pattern state 730, a left leg step state 732, a right leg step state 734, a left leg stair state 736, a right leg stair state 738 and an emergency fall state 740. The states 730-740 generate drive signals for one or more electrodes 750, numbered as Electrode #1 through Electrode #n in FIG. 7.

The user interface 704 may include the joystick 706 through which a user enters commands, or any other data entry device, including, for example, keypads, touch pads, dials, knobs, buttons, a microphone (with voice activation and processing capability), a trigger, or any other input device. The user interface 704 may also receive as input a signal from a module 104 within the neural prosthesis 100. This may be, for example, neural signals from the left leg sensor 708, neural signals from the right leg sensor 710, or one or more torso orientation signals from the torso sensor 712, which may be, for example, a three-dimensional accelerometer or other orientation sensor. Through these sensors 708-712, a user may provide input to the system by intentional movements of body parts where, for example a neural signal sensed at the left leg sensor 708 may be detected and used as a trigger to begin a stepping or stair climbing motion. The inputs may also operate autonomously, i.e., without conscious activation by a user. For example, the fall detection process 724 may detect a potential fall based upon a change in inclination of the torso, and initiate an emergency fall process 740 that overrides other processes. The emergency fall process 740 may, for example, slowly relax leg muscles to permit the user to slowly collapse to the ground. The fall detection process 724 may also activate the alarm 716.

The system on/off process 718 is initiated by activation of an on/off switch or other user input. The on/off process 718 may initialize hardware and software in the neural prosthesis 100 and pass control to the determine initial state process 720. The determine initial state process 720 may, for example read sensor and state data from modules 104 in the neural prosthesis 100 and determine an initial state for the neural prosthesis 100, as well as whether the user is in a safe position to use the system 700.

The menu process 722 may drive the user display 714 to display one or more options available to the user, among which the user may select, for example, by operation of the joystick 706. The menu process 722 may present options such as, for the leg control prosthesis of FIG. 6, standing, stepping, or climbing stairs. Upon selection of a menu item, control may be passed to one or more state control processes 726 which impress electrode stimulus patterns 730-740 onto electrodes to obtain the desired muscle activity.

Stimulus patterns 730-740 may be used in conjunction with sensor data. For example, where the nervous system responds to a foot touching ground, this signal may be detected and used to limit a stepping signal even where the nervous system signal does not reach a user's brain. Stimulus patterns 730-740 may also be regulated by further user input where, for example, a user may stop a stepping pattern through the joystick when a desired leg position has been reached.

It will be appreciated that details of the system, such as sensor placement, stimulus waveforms, and sequencing of actions may be highly dependent on an individual user's physiology and the desired motor function to be controlled. Specific stimulus patterns are thus not described in detail here, however stimulus patterns for muscle movements are well-characterized in the art, as shown for example in the following references, the teachings of which are incorporated herein by reference: Kobetic R, Marsolais E B. Veterans Affairs Medical Center, Cleveland, Ohio. Synthesis of paraplegic gait with multichannel functional neuromuscular stimulation. IEEE TRANSACTIONS ON REHABILITATION ENGINEERING (June 1994) 2; 2 (66-79); Popovic D, Stein R B, Oguztoreli M N, Lebiedowska M, Jonic S. IEEE. Optimal control of walking with functional electrical stimulation: a computer stimulation study. IEEE TRANSACTIONS ON REHABILITATION ENGINEERING (March 1999) 7; 1 (69-79); Skelly M M, Chizeck H J. Case Western Reserve University, Cleveland, Ohio, University of Washington, Seattle, Wash. Real-time gait event detection for paraplegic FES walking. IEEE TRANSACTIONS ON REHABILITATION ENGINEERING (March 2001) 9; 1 (59-68).

In the example system of FIG. 7, it is assumed, for example, that a user has voluntary control over arms sufficient to operate a joystick. If this were not the case, other user inputs could readily be adapted for user input.

It will be appreciated that other options can be provided to the user that are not described shown in FIG. 7. In each case, a stimulation pattern is developed and stored within the implanted neural prosthesis. In addition, there are other system parameters that can be accessed by the user and/or clinician that are not shown in the figure. For example, the charge state of the battery can be indicated to the user through the user display 714. The integrity of the electrodes may be monitored by the implanted system, and their status can be displayed to the user if necessary. Other information, such as the direct sensor outputs, can be obtained by a clinician or researcher as needed.

It will also be noted that control of the system may be distributed among various processes which may be located in a central controller at the bridge, or at modules distributed throughout the system. Thus in one aspect there is disclosed herein a distributed controller for use in a neural prosthesis.

It will be appreciated that the systems described herein may be adapted to a variety of neural prosthetic applications using the modules 104, communication medium 102, and bridge 400 described above. Thus the application of the invention is not limited to the specific examples above, nor is the application of the invention limited to motor neuroprosthetics. The following examples show other potential applications of the system.

Hand Function System. A C7 level spinal cord injury results in the loss of finger and thumb flexion. Electrical stimulation can be used to activate these paralyzed muscles to provide grasp and pinch force. Control of the stimulation of these muscles can be provided by activity of the wrist extensors, which are under voluntary control. Wrist extensor activity can be detected by recording the electro-myographic (EMG) signal. This can be implemented using the systems described above. A stimulator module may be placed to stimulate the finger and thumb flexors. An EMG electrode may be implanted on the extensor carpi radialis brevis (ECRB), and an EMG signal processing module may also placed in the forearm. These two units are networked. The recorded EMG signal may be converted into a signal and used to determine the user's desired stimulus levels for the six electrodes. Functionally, the user will find that as he extends his wrist, his hand will close, and he can open his hand by voluntary flexing his wrist and/or voluntarily extending his fingers and thumb.

Whole Arm Function System. Complete loss of arm function results from spinal cord injury at the C4 (or higher) level. Restoring function for these individuals requires stimulation of hand, arm and shoulder muscles in a coordinated fashion. User control of arm function is obtained by utilizing voluntary movements generated by the user's head and neck. Using the neural prosthetics described above, electrodes may be placed in the hand, forearm, arm, and chest. Sensor modules can be located in these regions of the body. Three muscle-based actuator modules and three nerve based actuator modules are used to stimulate 26 different muscles. Voluntary control is achieved by recording EMG from the frontalis, sterno-cleido-mastoid and trapezius muscles. Electro-oculogram (EOG) signals can also be recorded from the electrodes placed on the frontalis muscle, allowing eye movements to be used as an additional control input. Orientation sensors may be placed on the ulna, humerus and sternum, and provide feedback information regarding the position of the arm in space. Each module may be connected through the network to the bridge. The bridge may provide additional processing power for EMG signal acquisition and/or interpretation. This system may provide the user with hand and arm function.

Standing, Walking and Bladder/Bowel Function System. Spinal cord injury at the C8 through T12 level results in complete paralysis of the lower extremities, as well as loss of bowel, bladder and sexual function. Research has demonstrated that each of these functions can be restored using electrical stimulation. The systems described herein may be used to realize restoration of all of these functions with a single neural prosthesis. A total of 12 muscle-based or nerve-based electrodes may be used for each hip and knee flexion and extension, hip adduction and abduction, ankle plantar and dorsi-flexion, and extension. Three actuator modules with nerve cuff electrodes are placed on the S1, S2 and S3 dorsal roots to provide bladder, bowel and sexual function. Sensor modules with accelerometers may be placed on the hip, femur and tibia, and used to obtain information about leg position. Sensor modules with contact sensors may be placed in the sole of the foot to record floor impact. A bridge may provide centralized power to the system of networked modules. Processing capacity may be deployed within modules in the legs and/or provided centrally at the bridge. This system may restore an individual's ability to stand and take steps, and may concurrently be applied to restore bladder function, bowel function, and sexual function.

Hemiplegia Walking System. Hemiplegia can result from a stroke or incomplete spinal cord injury. Sensor modules placed in the normal leg can be used to control the electrical stimulation of the paralyzed leg to produce coordinated movements such as standing and walking. Sensor modules having EMG electrodes may be placed in the non-paralyzed leg to detect activity in the hip and knee muscles. Sensor modules that detect contact may be placed in both feet to identify specific stages of the gait cycle. In this system, signal processing may be performed at one or more of the sensor modules to provide real-time control of the affected limb.

Other Applications. The invention allows general input and output devices to be connected to a very flexible network providing communication and power. Therefore, various types of mechanical actuators, such as drug delivery pumps, could be included in this system. Chemical sensors can be incorporated into this system, for example providing devices that could sense the level of a particular drug or other circulating metabolic compound and use that signal to control the level of drug delivery through a miniature implanted pump. Other neural prosthetic systems, such as visual or cochlear prostheses would benefit from the existence of neural prosthesis capable of stimulation through various types of electrodes; and sensor modules. The clinical potential of the systems described herein is quite broad, extending well beyond neurological injuries.

Thus, having shown the preferred embodiments, one skilled in the art will realize that many variations are possible within the scope and spirit of the claimed invention. It is therefore the intention to limit the invention only by the scope of the following claims.

What is claimed is:

1. An implantable system comprising:
   a first neural prosthesis controlling a nervous system in a first region of a body;
   a second neural prosthesis controlling the nervous system in a second region of the body; and
   a controller connected in a communicating relationship with the first neural prosthesis and the second neural prosthesis, the controller coordinating a transfer of data between the first neural prosthesis and the second neural prosthesis to achieve a body function that combines the first region of the body and the second region of the body;
   wherein each prosthesis includes at least two modules implantable in living tissue, each module including at least one of a sensor or an actuator, each module also including a processor and a network interface which is configured to communicate with at least one other module; and
   a power source providing a data signal and a power signal to each module, each module obtaining power from and solely being powered by the power signal.

2. The system of claim 1 wherein the power source further provides a clock signal.

3. The system of claim 2 wherein the clock signal is a variable system clock signal modulated onto the power signal for controlling power consumption by one or more of the plurality of modules.

4. The system of claim 1 wherein the nervous system includes at least one of sensory nerves, motor nerves, and neural circuits.

5. The system of claim 1 wherein the data signal includes control information for at least one of the plurality of modules.

6. The system of claim 1 wherein the data signal is addressable to one or more selected ones of the plurality of modules.

7. The system of claim 1 wherein one of the plurality of modules modulates a data signal onto the power signal.

8. The system of claim 1 wherein the communicating relationship includes a data network having a data transmission rate of at least 100 kbps.

9. The system of claim 1 wherein the communicating relationship includes a wireless network.

10. The system of claim 1 wherein the body function includes walking.

11. The system of claim 1 wherein the body function includes a muscle contraction in the first region in response to a user-initiated movement detected in the second region.

12. The system of claim 1 further comprising one or more additional neural prostheses.

13. The system of claim 12 wherein the one or more additional neural prostheses are connected in a communicating relationship with the controller.

14. The system of claim 12 wherein the one or more additional neural prostheses are connected to the first neural prosthesis or the second neural prosthesis.

15. The system of claim 1, wherein each one of the plurality of modules is a biocompatible, implantable device that shares a communication medium, the plurality of modules grouped into one or more networks across the communication medium wherein modules in a network operate autonomously to control a body function; and
   comprising a controller that dynamically reallocates one or more of the modules among the one or more networks to perform a different body function.

16. The system of claim 15 wherein the controller is a programmable controller coupled to the communication medium.

17. The system of claim 15 wherein the controller is distributed among programmable processors operating on each one of the plurality of modules.

18. The system of claim 15 wherein more than one of the one or more networks share one of the plurality of modules.

19. The system of claim 15 wherein the communication medium includes at least two branches that are physically separated from one another by a bridge.

20. The system of claim 19 wherein at least one of the networks includes a from each of two or more of the at least two branches, control data within the at least one of the networks being communicated through the bridge.

21. The system of claim 1 wherein each prosthesis includes a plurality of modules implantable in living tissue, each module including at least one actuator, each module also including a processor and a network interface which is configured to communicate with at least one other one of the plurality of modules within the same prosthesis.

* * * * *